United States Patent [19]
Savjani

[11] Patent Number: 5,935,775
[45] Date of Patent: Aug. 10, 1999

[54] WHOLE BLOOD ANALYSIS OF PROSTATE SPECIFIC ANTIGEN SPOTTED ON A SOLID SUPPORT

[76] Inventor: Gopal V. Savjani, Diagnostic Systems Laboratories Inc., 445 Medical Center Blvd., Webster, Tex. 77598-4217

[21] Appl. No.: 08/626,641

[22] Filed: Apr. 2, 1996

[51] Int. Cl.[6] .............................. C12Q 1/00; C12Q 1/42; G01N 33/53
[52] U.S. Cl. .............................. 435/4; 435/968; 435/975; 435/21
[58] Field of Search ............................ 435/4, 7, 29, 975, 435/968, 21; 530/350; 128/760

[56] References Cited

U.S. PATENT DOCUMENTS

| | | | |
|---|---|---|---|
| Re. 33,405 | 10/1990 | Chu et al. ................................ | 530/350 |
| 4,267,272 | 5/1981 | Josephson .................................. | 435/4 |
| 5,190,049 | 3/1993 | Briggs et al. ........................... | 128/760 |

OTHER PUBLICATIONS

Ito et al; Japan J. Clin. Pathol.; vol. 42, pp. 539–543, 1994, Month not available. Please print.

Armbruster, "Prostate–Specific Antigen: Biochemistry, Analytical Methods, and Clinical Application," Clin. Chem. Feb. 1993, 39, 181–195, Month not available. Please print.

Watanabe H. et al., PSA Assay of Dried Blood Samples From the Ear Lobe on a Filter Paper with Special Reference to Prostatic Mass Screening, Prostate 27:90–94 (Aug. 1995).

Derwent WPI Abstract of JP 7098315A for Simple and Easy Determination of Prostate–specific Antigen—by Extracting Analyte Component Containing the Antigen from Part (s) of Support Holding Blood Components. (1995) Month not available.

*Primary Examiner*—Louise N. Leary
*Attorney, Agent, or Firm*—Jenkens & Gilchrist

[57] ABSTRACT

The present invention provides for the measurement of prostate specific antigen (PSA) from extracts of blood dried on a suitable solid support. PSA in solid support dried blood is stable for more than 100 days at room temperature. The procedure of the present invention can reliably distinguish normal from elevated levels of PSA and that facilitates screening and monitoring to detect disease in large scale mail-in programs to centralized laboratories.

20 Claims, 7 Drawing Sheets

WHOLE BLOOD ANALYSIS OF PROSTATE SPECIFIC ANTIGEN SPOTTED ON A SOLID SUPPORT

BACKGROUND OF THE INVENTION

1. Field of the Invention

The present invention relates to screening or testing for prostate specific antigen (PSA). More specifically, the present invention relates to a method for screening for PSA from whole blood spotted on a solid support. Additionally, the present invention relates to a test kit for screening or testing for PSA using the solid support.

2. Description of the Prior Art

Prostate adenocarcinoma accounts for the majority of malignancies in males over the age of 65. Yearly screening for prostate cancer is recommended after the age of 45. There has been considerable effort toward identifying suitable prostate cancer markers to assist in screening and diagnosing this disease.

PSA is recognized as the most sensitive marker of prostatic adenocarcinoma (Brawer M K. Cancer 1993; 71 (suppl):899–905; Oesterling J E. J Urol 1991; 145:907–23). PSA is also recognized as a proven screening vehicle (Gann P H, et al. J Amer Med Assoc 1995; 273:289–94.; Catalona W J, et al. JUrol 1994; 151:1283–90). It is the most sensitive front line test for identifying prostate gland-contained, and hence presumably curable, cancer. PSA is also useful in detecting clinically significant tumors, as opposed to latent, indolent microcarcinomas. In fact, screening for PSA is even superior to the common office practice of digital rectal examination (DRE). For example, Labrie et al. (Clin Invest Med 1993; 16: 425–39) showed that 97% of cancers detected at annual follow-up by DRE plus PSA testing were PSA-positive. Thus, only a minimal benefit accrues from including DRE in the medical evaluation.

Prostate specific antigen has also been used to detect the onset of puberty in children between ages 8 and 25 years (Vieira J. G. H., et al. J Clin Endocrinol Metab 1994;78: 1185–1187). Since PSA is an androgen-dependent protein and its expression is up-regulated by androgenic steroid hormones, women with hyperandrogenic syndromes may also have elevated PSA in their serum. Additionally, PSA has now been found in the serum and extracts from breast tumors (Diamandis E. P., Yu H. J Clin Endocrinol Metab 1995;80:1515–1517), indicating that it has utility in breast cancer screening and monitoring.

Currently, PSA is tested by first collecting a blood specimen via venipuncture phlebotomy. This usually necessitates that the individual to be tested make a physician office or hospital visit. The blood so collected is usually processed for shipment to a suitable clinical diagnostic laboratory. In most cases, shipment necessitates first freezing serum or plasma, and shipping (on ice) the frozen specimen to the diagnostic testing laboratory. Hence, any means to simplify collecting and testing blood would facilitate the screening for prostate disease, and facilitate earlier detection and treatment.

Blood collected by capillary puncture from the heel, finger, or earlobe and dried on filter paper has been used advantageously in large scale infant screening programs throughout the world to detect inborn errors of metabolism and congenital defects (Dussault J H, et al. J Pediatr 1974; 86:670–4). Such filter paper techniques provide a suitable delivery system alternative in cases where transport delays, safety concerns, and high temperatures preclude the shipment of liquid whole blood to the diagnostic testing laboratory. Also, capillary puncture is less invasive and more convenient than venipuncture. Additionally, only minimal volumes of dried blood need be collected in this approach.

There has not heretofore been a method for using dried whole blood to test PSA. Additionally, there has not heretofore been a device for collecting a specimen onto a solid support for convenient shipment to a diagnostic laboratory. These and other disadvantages of the prior art are overcome by the present invention.

SUMMARY OF THE INVENTION

In accordance with the present invention, a method of testing PSA in an individual is provided, wherein said method comprises the steps of collecting blood from an individual, applying said blood onto a solid support, extracting blood from said solid support with a buffer extract to form a blood extract, and testing said blood extract for PSA.

Also provided in the present invention is a method of diagnosing or monitoring disease comprising the steps of collecting blood from an individual, applying said blood onto a solid support, extracting blood from said solid support with a buffer extract to form a blood extract, and testing said blood extract for PSA.

In accordance with the present invention, also provided is a blood collection kit for measuring PSA comprising a solid support and a blood collection device.

These and other advantages of the present invention will become apparent from the following detailed description.

BRIEF DESCRIPTION OF THE DRAWINGS

FIG. 2. Stability of filter paper spotted PSA in whole blood. Panel A shows control I; Panel B shows control II; Panel C shows control III and Panel D shows control IV.

DETAILED DESCRIPTION OF THE INVENTION

According to the teachings of the present invention, whole blood collected from an individual is spotted onto a suitable solid support. The whole blood is collected via techniques known to those skilled in the art including, but not limited to, finger prick, thumb prick, heel prick, ear lobe prick or any other form of capillary puncture by which a blood specimen may be obtained. In an alternative embodiment, whole blood may be obtained by venipuncture and spotted onto the solid support. Preferably, the blood specimen is collected via finger prick or thumb prick. Suitable devices for conducting capillary puncture include, but are not limited to, lancets and needles. Suitable lancets include, but are not limited to Monolet® (Sherwood Medical, St. Louis, Mo., USA), tender foot® (Baxter, Miami, Fla., USA), Minilance®, Autolet®, Unilet®, and Microlance® (Becton Dickinson, Franklin Lakes, N.J., USA). The amount of whole blood required to be spotted onto the solid support is about 50 μL to about 200 μL, and preferably about 80 μL to about 100 μL. Accordingly, about 2 drops to about 4 drops may be spotted onto the solid support in accordance with the teachings of the present invention.

Any suitable form of solid support for collection may be used. A suitable solid support is one on which blood can be spotted and dried and from which PSA can later be extracted. Preferably the solid support is a paper medium, and more preferably it is filter paper such as used in newborn screening programs and which are known to those skilled in the art. These include, but are not limited to Schleicher and Scuell (Keene, N.H., U.S.A.) No. 903 filter papers. The S & S grade 903 filter paper is relatively thick and very absorbent, and applied drops of blood readily diffuse radially outward to form overlapping circles. It is the recognized standard for collecting dried blood, and the absorbency of each manufactured batch is kept within tight limits as certified by quality control testing carried out by the Centers for Disease Control and Prevention in Atlanta, Ga. (USA). This type of paper has been widely used in neonatal thyroid/phenylketonuria dried blood screening programs. In one embodiment, the solid support comprises a first area onto which blood is applied, and a second area for recordation of information about the blood donor. The second area need not have the absorbency of the first area, as blood will not be spotted onto the second area. Alternatively, the solid support comprises solely the first area described above. In such cases, information recordal can be conducted on a separate instrument.

After spotting, the blood is allowed to dry. Depending on ambient conditions, drying takes about one hour to about 3 hours, preferably about 2 hours. It is anticipated that the individual donor will be responsible for collecting the whole blood specimen, recording information about him or herself, and shipping the impregnated solid support to the diagnostic testing laboratory.

Analysis of PSA from the blood-impregnated solid support is conducted by first extracting PSA from the dried blood on the solid support. This may be accomplished by removing one or more sections from the blood-impregnated solid support. In an alternative embodiment, the entire blood-impregnated solid support may be subjected to extraction without removing one or more sections from said solid support. Those skilled in the art will know a suitable means of collecting such sections. Preferably, sections of about one (1) to about ten (10) millimeters diameter, and more preferably about six (6) to about seven (7) millimeters in diameter are removed from the blood-impregnated solid support. This may, for example, be conducted by using a single hole paper punch, but any other means for removing sections, such as knives or scissors, may be used.

The sections so removed, or, alternatively, the entire blood-impregnated solid support, are placed in a suitable container with an extraction buffer, and are incubated for a suitable time period in which the dried blood may be leached from the solid support and dissolved in the liquid phase. The extraction buffer may be distilled water, or it may be more complex. Preferably, the extraction buffer of the present invention comprises a protein and one or more suitable buffers. Preferably, these buffers are Tris buffers. Most preferably the extraction buffer comprises 0.05 mol/L Tris, pH 7.4 containing 60 g/L bovine serum albumin, 5 mL/L Tween 20 and 10 mL/L mouse serum. Suitable incubation times will be ascertainable by those skilled in the art. Preferably this includes a period of about 30 minutes to about two hours and most preferably about one hour at room temperature.

PSA can be analyzed by any suitable sensitive assay technique. These include but are not limited to techniques such as immunoradiometric assays, chemiluminescence immunoassays, electroluminescence techniques, fluoroimmunoassays, enzyme immunoassays or bioluminescence immunoassays. Both total PSA and non-$\alpha_1$-antichymotrypsin-bound (free) PSA can be tested. Free PSA, for example, can be tested using the technique described in Pettersson, K, et al. Clin Chem 1995;41 :1480–1488, incorporated by reference herein.

The method and kit of the present invention can be used to diagnose and/or monitor disease states in individuals. Specifically, the method can be used to diagnose disorders, such as prostate cancer, benign prostatic hyperplasia, prostatitis, breast cancer, and androgenic disorders and/or to monitor response to therapy and/or to monitor patients for possible relapse after radical prostatectomy.

The following examples serve to illustrate specific embodiments of the invention, but should not be considered as a limitation on the scope of the invention.

EXAMPLE 1

Spotting onto Solid Support, Extraction and Analysis of PSA from Dried Blood Spots Heparinized or otherwise anticoagulated whole blood, obtained by venipuncture, is spotted onto Schleicher and Schuell #903 filter paper and left to dry for at least 2 hours at room temperature. About 80–100 μL of blood is added per filter paper spot. The spotted papers are then stored in plastic bags at room temperature.

A commercially available, hand held, single hole paper puncher was used to punch three, 6 mm diameter paper disks impregnated with blood. It is preferred to cut one 6 mm disk per filter paper spot. Each patient was asked to donate 4 blood spots. From one filter paper blood spot at least two disks were cut. The three disks were placed in either a 12×75 mm glass tube or in the well of a 48- well culture plate. A 600 μL aliquot of the extraction buffer was added.

Extraction efficiency was investigated using a variety of extraction volumes, durations of extraction and different liquid media. In order to investigate the extraction efficiency of PSA from dried blood spots the following extraction buffers were used:

A) Distilled water.
B) 50 mol/L Tris, pH 7.80, 0.1 g/L sodium azide.
C) 10 mol/L Tris, pH 7.80, 9 g/L NaCl, 0.5 g/L Tween 20.
D) 50 mol/L Tris, pH 7.80,60 g/L bovine serum albumin (BSA), 5 mL/L Tween 20, 10 mL/L mouse serum and 0.1 g/L sodium azide
E) 50 mol/L Tris, pH 7.80, 60 g/L bovine serum albumin (BSA), 0.1 g/L sodium azide, 0.5 g/L Tween 20.
F) PSA assay buffer (50 mol/L Tris, pH 7.80, 60 g/L BSA, 10% goat serum, 10% mouse serum, 0.5 g/L Tween 20).

Extraction time varied between 15 min, 30 min, 1 h and 2 h. For this experiment, a spotted whole blood sample spiked to increase the PSA concentration to ~100 μg/L was used. The results are shown in Table 1. Clearly, any of the six buffers could be used to extract the PSA quantitatively within 15–30 min. For routine use, buffer D and 60 minute extraction time was selected. This procedure allows for the complete dissolution of blood PSA into the extraction buffer which is usually red in color due to lysis of red blood cells. This does not interfere with the analysis of PSA. The extract was analyzed for PSA.

TABLE 1

Extraction efficiency of PSA with varying extraction buffer and extraction time.

| Buffer* | PSA µg/L/Extraction Time | | | |
|---|---|---|---|---|
| | 15 min | 30 min | 1 hour | 2 hours |
| A | 149 | 123 | 145 | 105 |
| B | 165 | 153 | 140 | 130 |
| C | 119 | 125 | 127 | 138 |
| D | 117 | 121 | 118 | 129 |
| E | 100 | 102 | 118 | 129 |
| F | 125 | 125 | 108 | 120 |

*For description see text

The PSA concentration in the extract was determined using a highly sensitive immunoradiometric assay (PSA-IRMA). This assay kit is available from Diagnostic Systems Laboratories, Inc. in Webster, Tex., USA. The PSA-IRMA is equimolar (measures equally on a molar basis the PSA-$\alpha_1$, antichymotrypsin [PSA-ACT] complex and free PSA). The assay sensitivity when used for serum PSA is 0.003 µg/L and the dynamic range extends to 20 µg/L. A 200 µL sample was used and all measurements were conducted in duplicate.

EXAMPLE 2

Calibration of PSA Filter Paper Spot Assay

A system was devised which uses liquid PSA calibrators in 6% BSA. The PSA form in the calibrators is only free PSA, since the primary calibration material is purified seminal plasma PSA. A primary free PSA calibrator of 1,000 µg/L was used as follows: (a) a heparinized whole blood plasma sample was obtained from a healthy 45 year old female and tested for PSA with the PSA-IRMA. It was found to contain <0.003 µg/L of PSA and was considered the whole blood zero PSA calibrator; (b) aliquots of this blood were then spiked with purified seminal plasma PSA and allowed to equilibrate overnight at room temperature. These blood samples were analyzed by the PSA-IRMA to assign PSA values of µg of PSA per L of whole blood. Such standards, in the range of 0.5 to 100 µg/L were used to prepare filter paper spot standards. Spotting for such standards was conducted as described in Example 1.

The filter paper spotted standards were used as such to calibrate the PSA spot assay by extracting them in parallel with the samples. Alternatively, liquid PSA standards in 6% BSA were prepared as follows. Liquid PSA standards in 6% BSA in the range of 0.01–5 µg/L were prepared by diluting the stock PSA standard solution. These liquid standards were used as unknown samples in the assay in which the calibrators were filter paper spotted standards extracted as illustrated in Example 1. The apparent concentration of the liquid standards was calculated and used for calibrating assay runs in which filter paper spotted samples were analyzed. The calculated relationship between the nominal and apparent PSA concentration of the liquid PSA standards was as follows (average within the measuring range): Apparent PSA concentration=42×nominal PSA concentration. Table 2 shows nominal and apparent PSA concentration of the liquid standards calibrated against the blood spot standards.

TABLE 2

Nominal and apparent PSA concentration of liquid PSA standards used to calibrate the filter paper spot PSA assay.

| Nominal PSA Concentration, µg/L | Apparent PSA Concentration, µg/L |
|---|---|
| 0 | 0 |
| 0.012 | 0.5 |
| 0.024 | 1 |
| 0.048 | 2 |
| 0.12 | 5 |
| 0.24 | 10 |
| 0.60 | 25 |
| 2.38 | 100 |

The ratio of Nominal/Apparent of 42 underscores the fact that during filter paper spot extraction, the blood present in the three 6 mm disks was diluted to 600 µL volume of which only 200 µL was utilized for analysis (fraction 200/600=0.33). Also, the three 6 mm disks contained less than 200 µL of sample volume. Based on the ratio of 42, it was calculated that the three disks contained a total of approx. 30 µL of whole blood (of which ~50% is serum). The liquid standards prepared as described provided data identical to those of filter paper spotted standards and they were easier to prepare and use.

Figure 1:
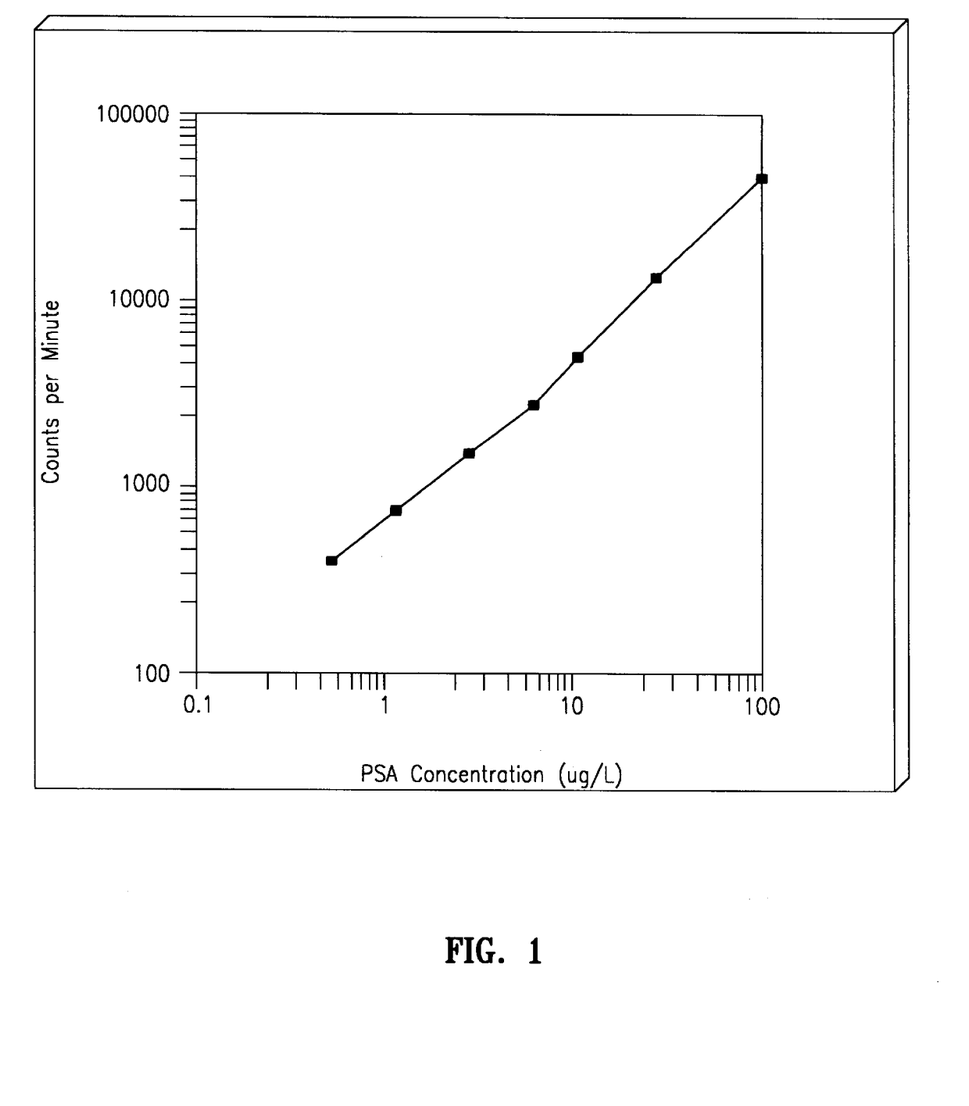
FIG. 1. Calibration curve using liquid calibrators.

The detection limit of the filter paper PSA assay calibrated as described was approximately 0.2 µg/L. A typical calibration curve using liquid standards is shown in FIG. 1.

EXAMPLE 3

Preparation of Quality Control Samples

Filter paper spotted quality control (QC) samples were prepared either in female whole blood or in goat or other animal blood spiked with seminal PSA. These QC materials, covering the range from 0.5–50 µg/L of PSA were analyzed in each run to monitor assay performance. The procedure for spiking and assigning values to these QC samples was illustrated by the procedures described in examples 1 and 2.

EXAMPLE 4

Reproducibility of PSA Determination from Blood Dried on Filter Paper

Multiple filter paper spotted whole blood QC samples were prepared and analyzed over a period of 30 days. The data are shown in Table 3.

TABLE 3

Day-to-Day precision of filter paper PSA assay

| QC Level | Mean PSA, µg/L | Standard Deviation | CV, % | Replicates * |
|---|---|---|---|---|
| 1 | 0 | 0 | — | 11 |
| 2 | 1.30 | 0.13 | 9.9 | 11 |
| 3 | 2.59 | 0.19 | 7.4 | 11 |
| 4 | 4.40 | 0.42 | 9.5 | 11 |
| 5 | 5.78 | 0.69 | 10.7 | 11 |
| 6 | 13.2 | 0.91 | 6.9 | 11 |
| 7 | 15.8 | 1.32 | 8.3 | 11 |
| 8 | 30.7 | 2.1 | 6.9 | 11 |

* over a period of 30 days.

It is clearly demonstrated that day-to-day precision was <11% over the normal, slightly elevated and highly elevated PSA concentrations in whole blood.

EXAMPLE 5

Stability of PSA

Figure 2A:
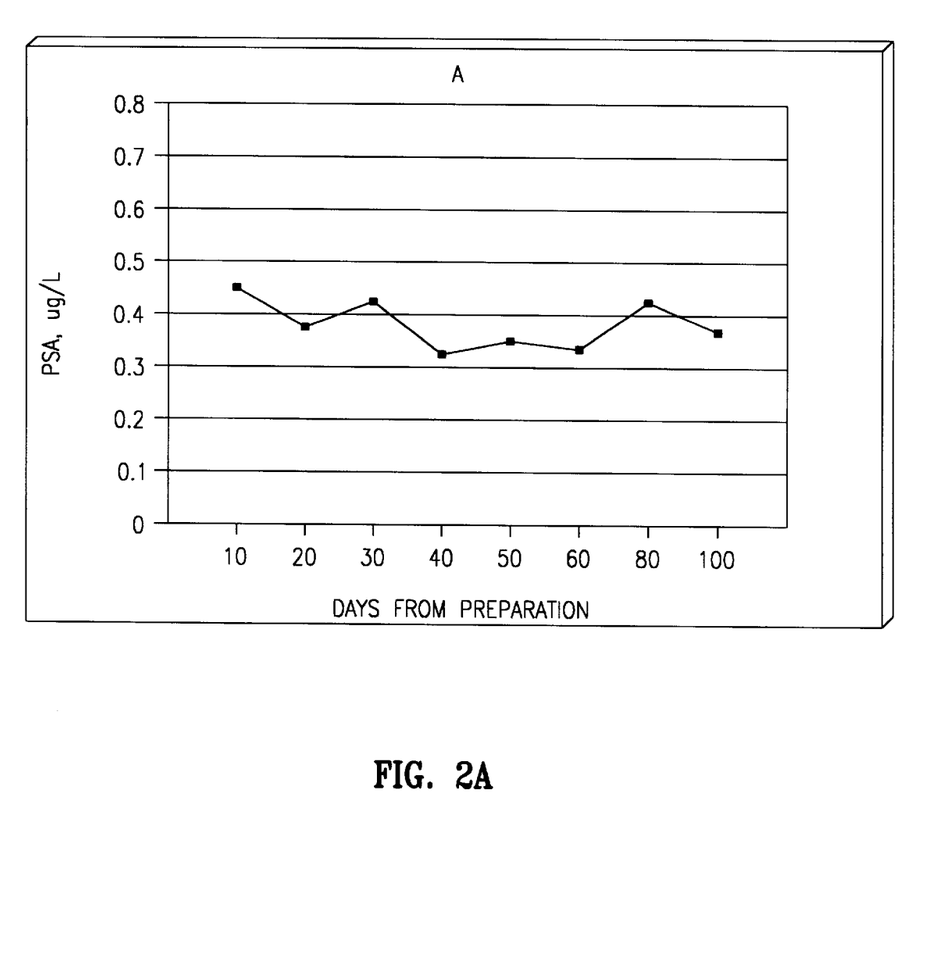
Figure 2B:
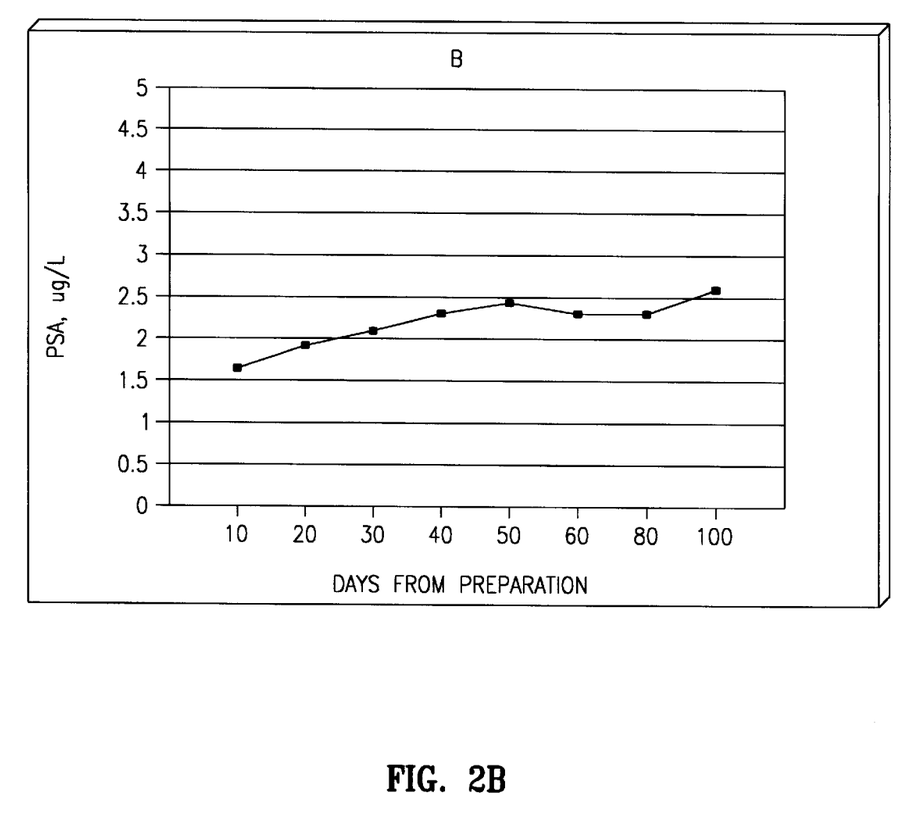
Figure 2C:
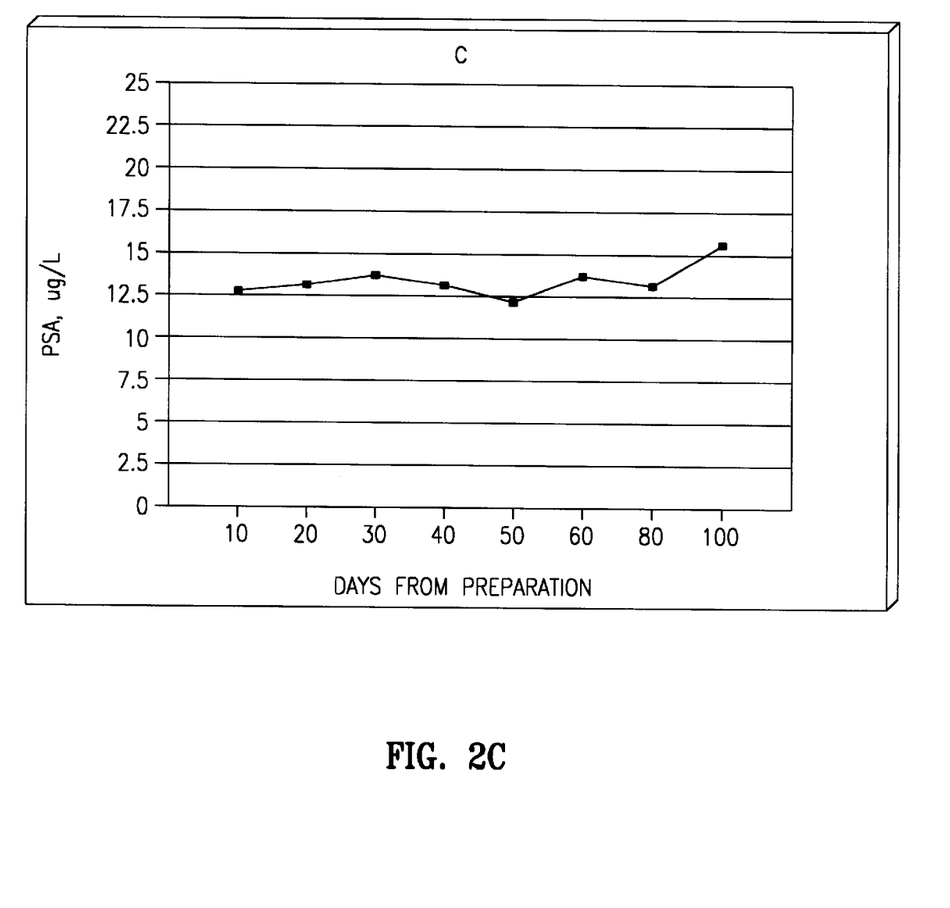
Figure 2D:
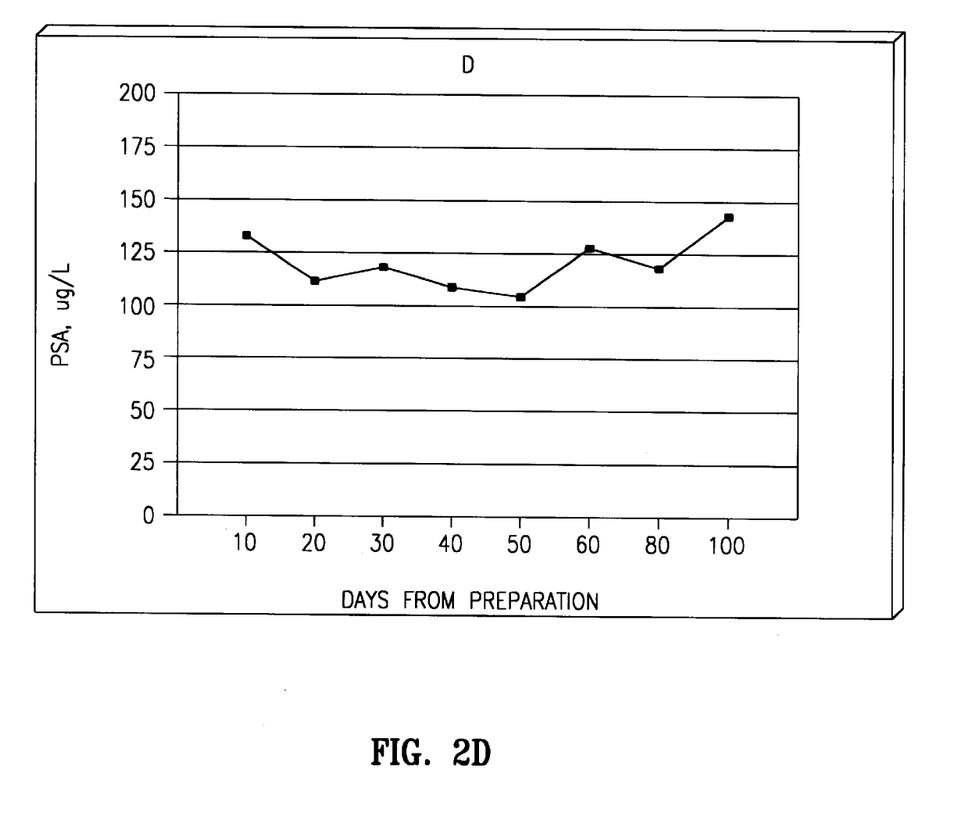

Filter paper controls containing four different levels of PSA were prepared as described in examples 1, 2 and 3, and stored at room temperature for up to 100 days. The samples were analyzed periodically to establish stability. Data are shown graphically in FIG. 2. Thus, control I (mean PSA= 0.41 µg/L, FIG. 2A), control II (mean PSA=2.1 µg/L, FIG. 2B), control III (mean PSA=13.7 µg/L, FIG. 2C) and control IV (mean PSA=117 µg/L, FIG. 2D) were not affected when stored at room temperature for up to 100 days, indicating that PSA levels in dried filter paper spots did not change appreciably with time.

EXAMPLE 6

Comparison of PSA in Serum and Corresponding Dried Blood

Figure 3:
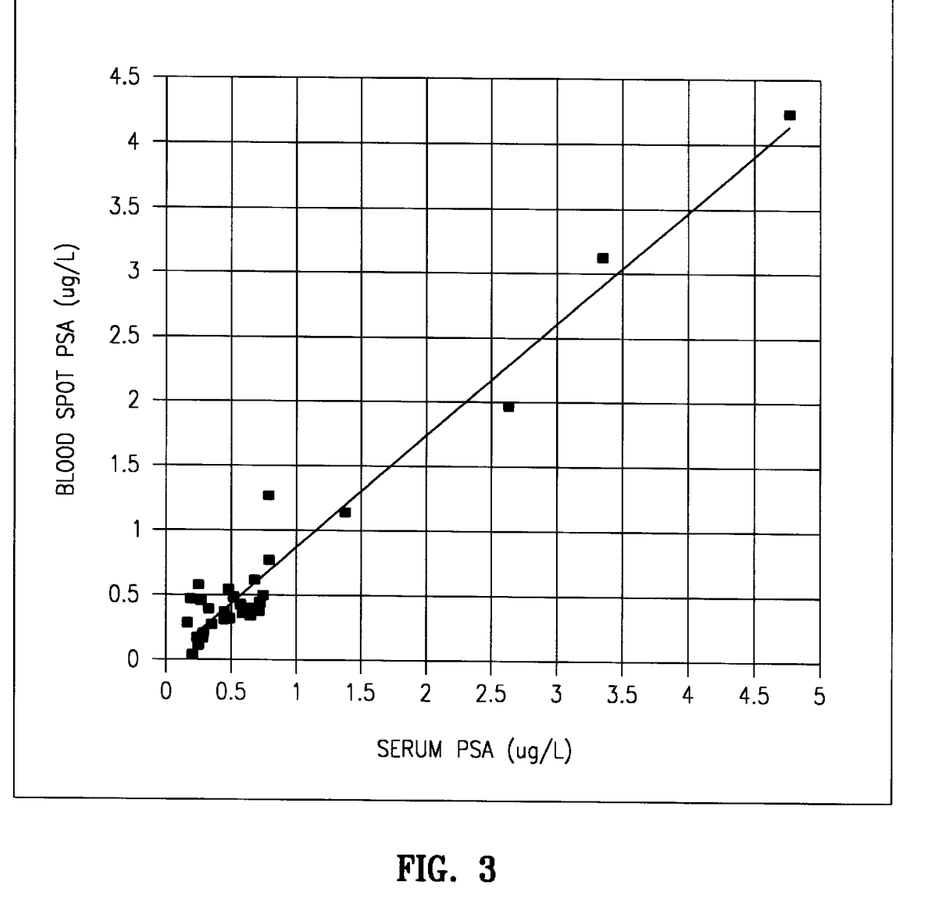
FIG. 3. Correlation between serum PSA and blood spotted PSA from the same individuals. Y (Blood Spot PSA)=0.88× (Serum PSA)+0.003, r=0.98 (n=33).

Venous blood was collected by phlebotomy and capillary blood by finger prick from 33 men. The venous blood was centrifuged to obtain serum and the finger prick blood was spotted on filter paper. Serum PSA and blood spot PSA were measured with the PSA-IRMA method. The data are shown in FIG. 3. There is an excellent correlation and agreement between serum PSA and blood spot PSA. The regression equation is: y (blood spot PSA)=0.88×(serum PSA)+0.003, r=0.98

These data support the view that serum PSA and filter paper PSA are equivalent in terms of clinical information related to levels of PSA in individuals blood. The good correlation extends from the normal range to increased levels of PSA.

EXAMPLE 8

Reference Range

Filter paper spotted blood was collected from 440 individuals of various ages who also answered a questionnaire of general health status and a more focused questionnaire on the presence of urologic disease. From this population 7 individuals were excluded due to history of prostatitis, 18 were excluded due to history of benign prostatic hyperplasia and 7 were excluded since they had undergone transurethral radical prostatectomy (TURP). Another 6 individuals were excluded since they reported urologic problems which they could not define. The distribution of values for the rest of the individuals (n=402) is shown in Table 4. As evident from this table, the reference ranges increase with age of the patients.

EXAMPLE 8

Clinical Studies

Figure 4:
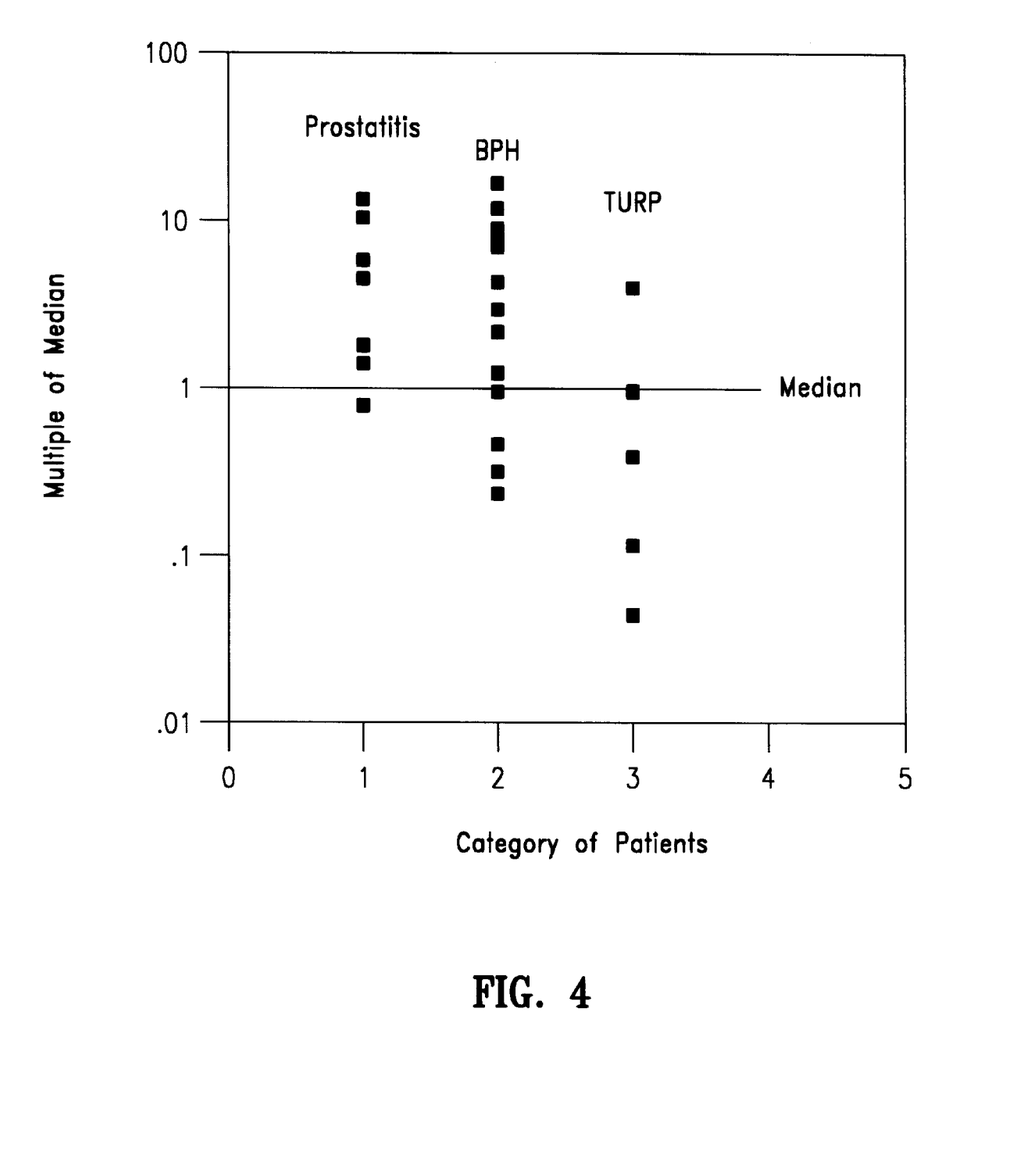
FIG. 4. Distribution of PSA expressed as multiple of median versus the patient categories shown. Patients with prostatitis and benign prostatic hyperplasia (BPH) generally have high PSA levels and patients with transurethral radical prostatectomy (TURP) generally have low PSA levels.

The data obtained with the patients who had positive history of urological disease are shown in Table 5 and in FIG. 4.

TABLE 5

Filter paper spot blood PSA in patients with positive history of urological disease.

| Disease | Age | PSA, µg/L | Percentile | Multiple of Median |
|---|---|---|---|---|
| Prostatitis | 37 | 0.36 | 75 | 1.50 |
| " | 41 | 0.61 | 79 | 1.60 |
| " | 45 | 1.6 | 97 | 4.2 |
| " | 51 | 0.39 | 44 | 0.91 |
| " | 54 | 4.2 | 100 | 9.8 |
| " | 62 | 4.5 | 100 | 11.5 |
| " | 78 | 2.6 | 93 | 4.7 |
| BPH | 43 | 0.50 | 68 | 1.3 |
| " | 46 | 0.40 | 52 | 1.05 |
| " | 61 | 1.9 | 91 | 4.8 |
| " | 65 | 0.20 | 36 | 0.51 |
| " | 66 | 0.10 | 26 | 0.26 |
| " | 67 | 3.9 | 99 | 10.0 |
| " | 69 | 1.4 | 86 | 2.5 |
| " | 72 | 3.9 | 100 | 7.1 |
| " | 75 | 2.7 | 94 | 4.9 |
| " | 73 | 9.1 | 100 | 9.3 |
| " | 72 | 2.7 | 94 | 4.9 |
| " | 76 | 1.8 | 85 | 3.3 |
| " | 79 | 4.2 | 100 | 7.6 |
| " | 80 | 0.70 | 65 | 1.3 |
| " | 82 | 4.4 | 100 | 8.0 |
| " | 84 | 0.20 | 20 | 0.36 |
| " | 90 | 0.60 | 56 | 1.09 |
| " | 70 | 6.9 | 100 | 12.5 |
| TURP | 62 | 0.04 | 19 | 0.10 |
| " | 65 | 0.02 | 17 | 0.05 |
| " | 68 | 1.45 | 88 | 3.7 |
| " | 68 | 1.45 | 88 | 3.71 |
| " | 72 | 0.10 | 16 | 0.18 |
| " | 78 | 0.00 | 0 | 0 |
| " | 82 | 0.00 | 0 | 0 |
| " | 71 | 0.21 | 23 | 0.38 |

In general, patients with prostatitis had PSA levels exceeding the 90th percentile of their age-matched controls. Also, many patients with BPH were found to have PSA levels exceeding the 90th percentile of their age-matched controls in accordance with previous data by others showing increased levels of PSA in patients with BPH (Oesterling J E, J Urol 1991; 145: 907–23).

As expected, patients with TURP generally have low PSA levels with the exception of one patient (FIG. 4).

TABLE 4

Reference Ranges for filter paper PSA in whole blood

| Age Group | Number of Patients | Percentile, PSA µg/L | | | | | | | | Mean | SD |
|---|---|---|---|---|---|---|---|---|---|---|---|
| | | 0 | 10 | 25 | 50 | 75 | 90 | 95 | 100 | | |
| <40 | 85 | 0 | 0.05 | 0.13 | 0.24 | 0.37 | 0.78 | 0.88 | 2.2 | 0.32 | 0.32 |
| 40–49 | 103 | 0 | 0.16 | 0.25 | 0.38 | 0.57 | 1.08 | 1.46 | 3.0 | 0.53 | 0.51 |
| 50–59 | 74 | 0 | 0.10 | 0.25 | 0.43 | 0.82 | 1.57 | 2.11 | 4.0 | 0.71 | 0.99 |
| 60–69 | 78 | 0 | 0 | 0.11 | 0.39 | 1.04 | 1.69 | 2.96 | 4.3 | 0.70 | 0.90 |
| 70+ | 62 | 0 | 0.04 | 0.23 | 0.55 | 1.06 | 2.46 | 2.84 | 3.6 | 0.87 | 0.92 |
| Total | 402 | | | | | | | | | | |

EXAMPLE 9

Case Reports

This example demonstrates case reports of the use of the PSA blood spot.

In case number 1, an 82 year old male, with a history of serum PSA values from 6–7 μg/L (measured by a commercial kit) over last few years but with a normal digital rectal examination (DRE) and ultrasound. The blood spot PSA was found to be 4.4 μg/L. This shows that PSA levels measured using the blood spot technique agrees with levels measured previously by an established commercial method.

In case number 2, a 75 year old male, with a history of serum PSA from 4.5–5.5 μg/L (measured by a commercial kit) the last 4 years but with normal DRE and ultrasound. The blood spot PSA was found to be 4.4 μg/L. This shows that PSA levels measured using blood spot technique agree with levels measured previously with an established commercial method.

In case number 3, a 73 year old male, had a serum PSA of 6.9 μg/L (measured by a commercial kit), Biopsy confirmed benign prostatic hyperplasia (BPH). His blood spot PSA was found to be 5.1 μg/L. These results show that there is good agreement between the clinical diagnosis and PSA levels measured using blood spot technique.

In case number 4, a 57 year old male had a history of serum PSA around 5–6 μg/L (measured by a commercial kit) with normal DRE and ultrasound. His blood spot PSA was found to be 2.2 μg/L. These results show that the blood spot PSA is in better agreement with clinical diagnosis than the previously measured PSA levels by a commercial kit.

What is claimed is:

1. A method of testing PSA in an individual comprising the steps of:
   (a) collecting blood from an individual;
   (b) applying said blood onto a solid support;
   (c) extracting said blood from said solid support with a buffer extract to form a blood extract; and
   (d) testing said blood extract for PSA,
   wherein said buffer extract comprises a buffer and protein.

2. The method according to claim 1, wherein said blood collecting step is conducted by capillary puncture.

3. The method according to claim 2 wherein said capillary puncture is selected from the group consisting of finger prick, thumb prick, or ear lobe prick.

4. The method according to claim 1, wherein said solid support is a paper medium.

5. The method according to claim 4 wherein said paper medium is filter paper.

6. The method according to claim 1, wherein said extraction step is conducted for a period of about thirty minutes to about two hours.

7. The method according to claim 1, wherein said extraction step is conducted for a period of about one hour.

8. The method according to claim 1, wherein said buffer extract comprises Tris, Tween 20 and serum albumin.

9. The method according to claim 1, wherein PSA is total PSA or free PSA, or both.

10. The method according to claim 1, wherein said testing said blood extract is a technique selected from the group consisting of immunoradiometric assays, chemiluminescence immunoassays, electroluminescence techniques, fluoroimmunoassays, enzyme immunoassays, or bioluminescence immunoassays.

11. A method of diagnosing or monitoring diseases characterized by variant levels of PSA, comprising the steps of:
   (a) collecting blood from an individual;
   (b) applying said blood onto a solid support;
   (c) extracting said blood from said solid support with a buffer extract to form a blood extract; and
   (d) testing said blood extract for PSA,
   wherein said buffer extract comprises a buffer and protein.

12. The method according to claim 11, wherein said blood collecting step is conducted by capillary puncture.

13. The method according to claim 12 wherein said capillary puncture is selected from the group consisting of finger prick, thumb prick, or ear lobe prick.

14. The method according to claim 11, wherein said solid support is a paper medium.

15. The method according to claim 14 wherein said paper medium is filter paper.

16. The method according to claim 11, wherein said extraction step is conducted for a period of about thirty minutes to about two hours.

17. The method according to claim 11, wherein said extraction step is conducted for a period of about one hour.

18. The method according to claim 11, wherein said buffer extract comprises Tris, tween-20 and serum albumin.

19. The method according to claim 11, wherein PSA is total PSA or free PSA, or both.

20. The method according to claim 11, wherein said disease is selected from the group consisting of prostatitis, benign prostatic hyperplasia, prostate cancer, androgenic disease, or breast cancer.

* * * * *